US00PP33650P2

(12) United States Plant Patent
Read et al.

(10) Patent No.: US PP33,650 P2
(45) Date of Patent: Nov. 16, 2021

(54) ***GAILLARDIA* PLANT NAMED 'SUNSET HALO'**

(50) Latin Name: ***Gaillardia* x *grandiflora***
Varietal Denomination: Sunset Halo

(71) Applicants: Charles Richard Read, Bognor Regis (GB); Jennifer Muriel Lintott, Bognor Regis (GB)

(72) Inventors: Charles Richard Read, Bognor Regis (GB); Keith George Lintott, Bognor Regis (GB)

( * ) Notice: Subject to any disclaimer, the term of this patent is extended or adjusted under 35 U.S.C. 154(b) by 0 days.

(21) Appl. No.: 17/173,658

(22) Filed: Feb. 11, 2021

(51) Int. Cl.
*A01H 5/02* (2018.01)
*A01H 6/14* (2018.01)

(52) U.S. Cl.
USPC ..... Plt./431

(58) Field of Classification Search
USPC ..... Plt./263.1, 431
See application file for complete search history.

*Primary Examiner* — Susan McCormick Ewoldt
*Assistant Examiner* — Karen M Redden
(74) *Attorney, Agent, or Firm* — Weatherly IP Solutions, LLC; James M. Weatherly

(57) ABSTRACT

A new cultivar of *Gaillardia* named 'Sunset Halo' that is distinguishable by a compact and dense plant habit and large brightly bicolored inflorescences which are red in their centers with a wide outer yellow ring is disclosed.

2 Drawing Sheets

Genus and species: *Gaillardia* x *grandiflora*.
Variety denomination: 'Sunset Halo'.

BACKGROUND

The present disclosure relates to a new and distinct cultivar of *Gaillardia* plant, also known as a blanket flower, an herbaceous perennial that is grown for use as an ornamental landscape and container plant. The new variety is known botanically as *Gaillardia* x *grandiflora* and will be referred to hereinafter by the variety name 'Sunset Halo'. *Gaillardia* is in the family Compositae, under which the commonly referred to "flower" is actually the inflorescence, and made up of smaller ray florets and disc florets. The ray florets themselves have the appearance of "petals".

'Sunset Halo' originated and was selected from a large population of hybrid seedlings from a *Gaillardia* breeding program started in 2006. The breeding program was conducted in a greenhouse nursery in West Sussex, United Kingdom. The aims of the breeding program were to produce novel combinations of flower colors and flower forms which are borne on well-branched plants with sturdy growth habits. The inventors carried out a controlled hybridization using combinations of selected named varieties and selected unnamed and unreleased seedlings retained from previous breeding cycles. 'Sunset Halo' was selected in 2013 for its large flowers comprised of two rows (layers) of bicolored (two-thirds red and one-third yellow) ray florets. 'Sunset Halo' flowers continually from spring until fall. 'Sunset Halo' was also selected for its compact and dense branching habit and its short flower stems.

The hybridization which led to the selection of 'Sunset Halo' was carried out during 2012 using a proprietary unreleased seedling known as '1051-1' (unpatented) as the male parent and a proprietary unreleased seedling known as '1039-1' (unpatented) as the female parent.

'Sunset Halo' was first asexually propagated in September 2014 in a greenhouse at the inventors nursery in West Sussex, United Kingdom using shoot cuttings taken from lateral branches. 'Sunset Halo' has been proven stable and to reproduce true to type in successive generations of asexual reproduction.

SUMMARY

The following traits have been repeatedly observed and represent the distinguishing characteristics of 'Sunset Halo'. 'Sunset Halo' has not been tested under all possible conditions and phenotypic differences may be observed with variations in environmental, climatic, and cultural conditions, without however, any variance in genotype.

1. 'Sunset Halo' exhibits a compact and dense branching plant habit.
2. 'Sunset Halo' exhibits single inflorescences composed of two close layers of flat ray florets.
3. The ray florets are markedly bicolored red and yellow, that is red towards the base and yellow towards the apex such that the whole inflorescence appears to have a bright yellow outer ring or halo.
4. The disc of 'Sunset Halo' is deep red in color when the inflorescence is fully expanded.
5. 'Sunset Halo' blooms continually from early spring until late fall.
6. 'Sunset Halo' is very floriferous over a long blooming period.
7. After one year's growth in a 3-liter container, 'Sunset Halo' is 30 cm to 35 cm in height and 35 cm to 40 cm in width.
8. 'Sunset Halo' is hardy in USDA zone 5.

DESCRIPTION OF THE PHOTOGRAPHS

The accompanying color photographs illustrate the overall appearance of the new *Gaillardia* cultivar 'Sunset Halo' showing the colors as true as it is reasonably possible to obtain in colored reproductions of this type. Colors in the photographs may differ from the color values cited in the detailed botanical description, which more accurately describes the actual colors of the new variety 'Sunset Halo'.

DESCRIPTION OF THE NEW VARIETY

Figure 1:
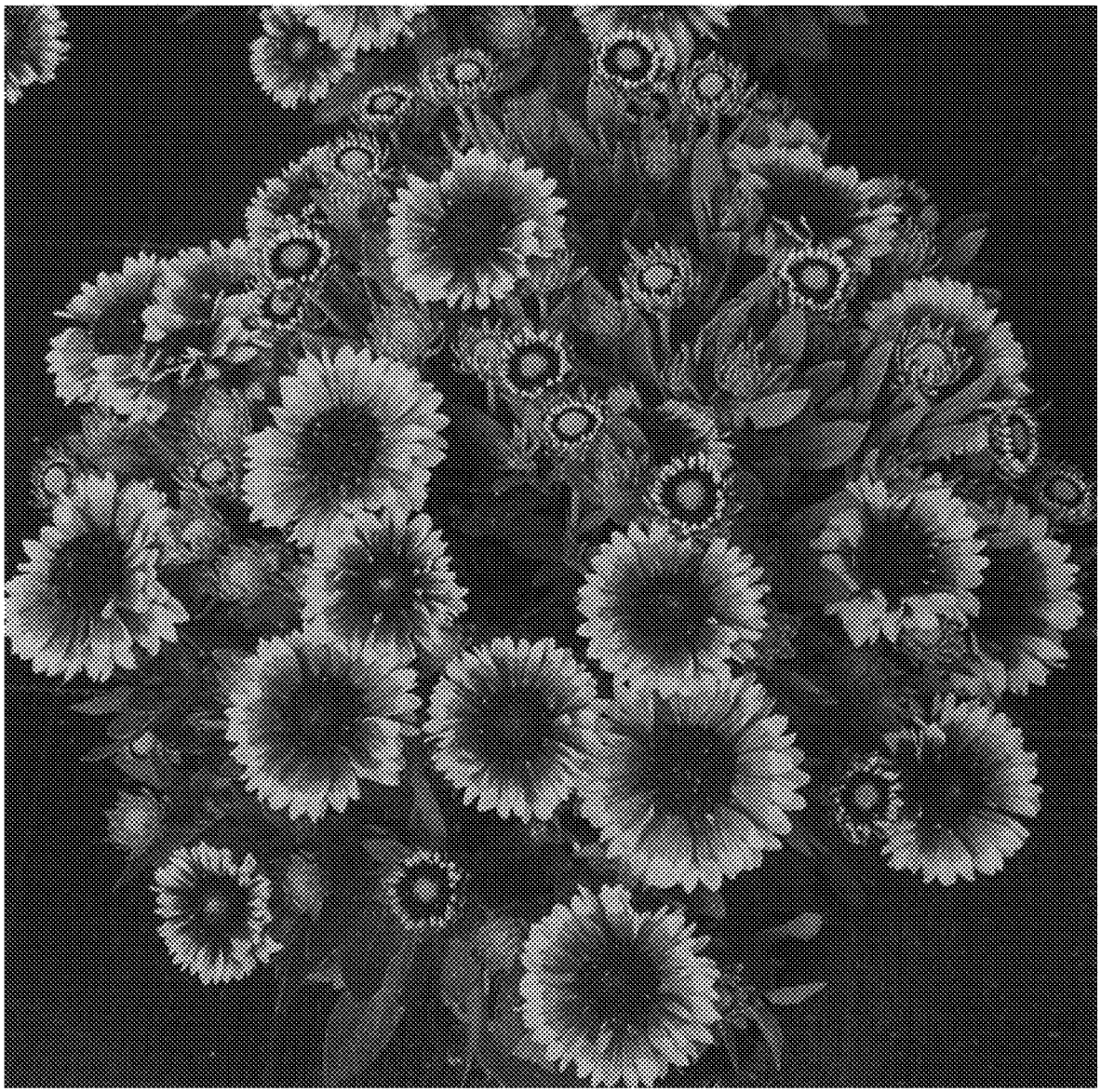
FIG. 1 depicts a whole plant of 'Sunset Halo' which has been grown in a frost-free greenhouse in West Sussex, United Kingdom. The illustrated plant is one year old and has been grown without any pinching or chemical growth regulator.
Figure 2:
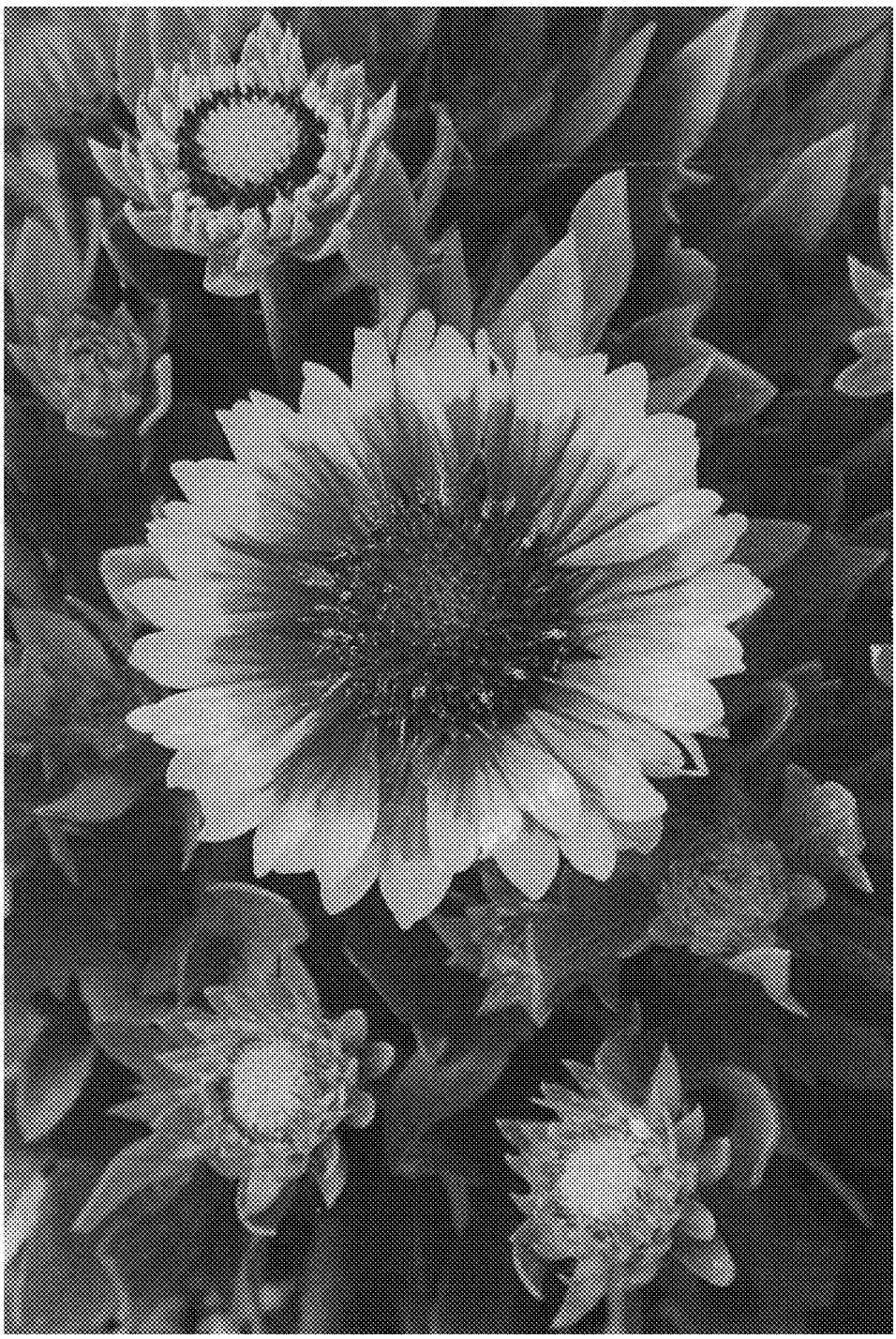
FIG. 2 depicts a close-up view of the fully expanded inflorescence of 'Sunset Halo'.

The following detailed descriptions set forth the distinctive characteristics of 'Sunset Halo'. Observations, measurements, values, and comparisons were collected in August 2020 in Santa Barbara, Calif. from a one year old plant grown outdoors in full sun in freely drained proprietary peat-based potting soil. Color determinations were made in accordance with The 2007 Royal Horticultural Society Colour Chart from London England, except where general color terms of ordinary dictionary significance are used.

Classification:

*Family*.—Compositae.

*Genus*.—*Gaillardia*.

*Species*.—X *grandiflora*.

*Common name*.—Blanket flower.

Parentage:

*Female parent*.—*Gaillardia* code number '1039-1' (unpatented).

*Male parent*.—*Gaillardia* code number '1051-1' (unpatented).

Plant:

*Propagation method*.—Softwood cuttings.

*Root system*.—Fine and fibrous.

*Vigor*.—Moderate vigor.

*Time to initiate roots*.—Approximately 14 to 20 days are needed to develop roots on initial cuttings.

*Temperatures to initiate rooting*.—The recommended air temperature is 20-21° Centigrade.

*Crop time*.—Approximately 10 weeks to 2 months are needed to produce a finished 15 cm diameter container plant from a rooted cutting.

*Growth habit*.—Compact and naturally freely branching.

*Suggested container size*.—15 cm container.

*Use*.—Ornamental for use as a landscape plant or container plant.

*Type*.—Herbaceous perennial.

*Plant dimensions*.—After one year's growth in a 3-liter container: 30 cm to 35 cm in height and 35 cm to 40 cm in width.

*Cultural requirements*.—Grow in full sun with moderate water, and well-draining soil such as loam.

*Hardiness*.—USDA Zone 5.

*Growing requirements*.—If grown outside in regions which experience winter freezing, 'Sunset Halo' may be started as a cutting during the spring or summer of the previous year, planted out prior to the onset of winter, and flowering will commence typically in May or June according to the region and season. When grown outside in frost-free regions, or in frost-protected greenhouses, 'Sunset Halo' will flower virtually all year round and may be started as a cutting (which should be non-flowering) at any time of year.

*Pinching*.—Plants may be pinched or stopped at approximately 5 cm to 8 cm above soil level in order to encourage prolific lateral branching.

Stems:

*Branching habit*.—Prolific branching after initial pinch.

*Stem color*.—141C.

*Stem length*.—Basal stem below first branch: 5 cm to 8 cm depending on height of pinch. Lateral branches: 8 cm to 12 cm.

*Stem diameter*.—5 mm to 6 mm (basal stem), 4 mm (lateral stems).

*Stem shape*.—Cylindrical, slightly fluted longitudinally.

*Stem surface*.—Markedly villous with dense coverage of very fine silvery hairs, approximately 3 mm to 4 mm in length.

*Internode distance* (*average*).—2 cm.

Foliage:

*Type*.—Evergreen.

*Leaf arrangement*.—Alternate.

*Margin*.—Entire.

*Leaf shape*.—Oblanceolate.

*Leaf dimensions*.—7.0 cm in length, 1.5 cm in width.

*Leaf base*.—Truncate.

*Leaf apex*.—Acute.

*Leaf attachment*.—Sessile.

*Leaf color* (*both surfaces*).—141C.

*Leaf venation pattern*.—Pinnate.

*Vein color* (*both surfaces*).—As leaf, 141C, except midrib lighter (both surfaces) 138D.

*Leaf surface* (*both surfaces*).—Pubescent, very fine silvery hairs, lighter than 156D, approximately 3 mm in length.

*Fragrance*.—A slight sage-like scent when bruised.

Inflorescence:

*Inflorescence*.—Solitary.

*Aspect*.—Facing upward.

*Dimensions of inflorescence*.—70 mm in diameter and 15 mm in height.

*Inflorescence type*.—Radiate capitate with central disc.

*Disc diameter* (*inflorescence fully expanded*).—26 mm.

*Inflorescence number per plant*.—A one-year old plant bears approximately 35 to 40 open and opening inflorescences, and 15 to 20 buds (green, prior to coloring) at one time.

*Blooming season*.—Spring, summer and fall.

*Lastingness of inflorescence on the plant*.—7 days, reducing to 4 days in full sun in mid-summer.

Peduncle:

*Peduncle dimensions*.—5 cm to 8 cm in length and 2.0 mm in diameter.

*Peduncle shape*.—Cylindrical.

*Peduncle surface*.—Surface is pubescent and exhibits longitudinal ridges.

*Peduncle color*.—141C where unexposed beneath the plant canopy, becoming 182B where exposed to direct sunlight.

*Peduncle strength*.—Stiff.

Flower buds:

*Bud shape*.—Globular whorl.

*Bud dimensions* (*before opening and coloring*).—15 mm in diameter and height.

*Bud color*.—141C.

*Bud surface*.—Villous.

Ray florets:

*Shape*.—Cuneate.

*Surface texture*.—Adaxial surface: Pubescent. Abaxial surface: Glabrous.

*Arrangement*.—Radiate, arranged in two close layers.

*Number of ray florets per inflorescence*.—45 to 55.

*Margins of ray florets*.—Entire.

*Dimensions*.—22 mm to 25 mm in length including the corolla tube, 7 mm in width at the widest point.

*Apex*.—Rounded, occasionally notched (2 or 3 notches), notch depth up to 3 mm.

*Base*.—Truncate.

*Corolla tube dimensions*.—5 mm in depth and 0.5 mm in diameter.

*Ray floret color* (*both surfaces*).—Red 46C to 46D for two-thirds of length from the base and yellow 6A for one-third of length from the apex.

*Ray floret veins* (*both surfaces*).—Longitudinal, parallel, fine but prominent, visible in petal blade as darker red 46C, not visible in yellow lobes.

*Self-cleaning or persistent*.—Self-cleaning.

Disc florets:

*Quantity of disc florets per inflorescence*.—Numerous, approximately 200 to 250.

*Disc floret dimensions* (*including pistil length*).—9 mm in length and 2.5 mm in width.

*Depth of disc floret corolla tube*.—6 mm.

*Surface of disc florets*.—Lanate.

*Color of disc florets* (*inflorescence fully expanded, both surfaces*).—46D.

*Phyllary*.—Dimensions: 5.50 cm in diameter and 3 cm in length. Color: 147B. Arrangement: Whorl.

*Involucral bracts*.—Number: An average of 25 per inflorescence. Shape: Oblanceolate. Dimensions: 2 cm in length and 0.50 cm in width. Margin: Entire. Apex: Acute. Base: Truncate. Color (both surfaces): 141C. Surface texture (both surfaces): Pubescent.

*Fragrance of inflorescence*.—Sweet honey-like.

Reproductive organs:

*Stamens* (*present on disc florets only*).—Number: Three, adnate to inner surface of corolla tube. Dimensions: 0.2 mm in width and 5 mm in length. Color: 17A. Form: Plumose. Anther: Dimensions: 0.50 mm in length and 1 mm in width. Color: 187A. Shape: Narrow lanceolate. Pollen: Present. Quantity: Large amount. Color: 17C.

*Pistil* (*present on ray florets and disc florets*).—Number: One per floret. Length: 12 mm. Style dimensions: 2 mm in length and 1 mm in width. Style color: 150D. Stigma: Dimensions: 8 mm in length and 1.75 mm in width. Form: Plumose. Color: 187A. Shape: Bifurcate. Ovary: Position: Inferior. Color: 150D. Shape: Globose. Dimensions: 1 mm in width and 2 mm in height.

Seeds:

*Number of seeds*.—Small to moderate amount (ranges from 50 to 100 seeds per inflorescence.

*Seed dimensions*.—5 mm to 6 mm in length (including hairs at apex) and 1 to 2 mm in diameter.

*Seed color*.—200A.

*Seed shape*.—Conical with rounded base and apex.

*Seed surface*.—Smooth except at apex where many very fine silver hairs, up to 2 mm in length, are present in circular groups.

Disease and pest susceptibility: 'Sunset Halo' has not been observed to exhibit any resistance to any particular pest or disease. 'Sunset Halo' is susceptible to downy mildew and to thrips as may be typical of *Gaillardia*.

COMPARISON WITH PARENTAL LINES AND KNOWN VARIETY

Whereas both parent varieties bear bicolored red and yellow inflorescences. The inflorescences of 'Sunset Halo' are brighter and more sharply contrasting with a wider concentric yellow outer ring. 'Sunset Halo' also exhibits a more compact and dense growth habit than either parent.

The variety of *Gaillardia* which is considered to most closely resemble 'Sunset Halo' is the inventors' variety *Gaillardia* 'Sunset Cutie' (U.S. Plant Pat. No. 26,970). The inventors consider that 'Sunset Halo' is a marked commercial improvement on 'Sunset Cutie' in that 'Sunset Halo' is shorter and more dense in habit, and bears flowers (inflorescences) which are brighter in color, with a wider yellow outer ring.

We claim:

1. A new and distinct cultivar of *Gaillardia* plant named 'Sunset Halo' as described and illustrated herein.

* * * * *